United States Patent

Brooks, III et al.

Patent Number: 5,254,472
Date of Patent: Oct. 19, 1993

[54] ORGANIC DIGESTING SYSTEM

[76] Inventors: Edward H. Brooks, III; Johnathan A. Brooks, both of 55 Acadia Dr., Rockland, Me. 04841

[21] Appl. No.: 840,180

[22] Filed: Feb. 24, 1992

[51] Int. Cl.⁵ .................................. C12M 1/10
[52] U.S. Cl. ............................ 435/312; 435/315; 435/316; 422/184; 422/209
[58] Field of Search ............ 435/287, 312, 313, 315, 435/316, 813, 299, 311; 422/184, 209, 210; 34/60, 61, 12, 135, 136, 137; 241/74, 18, 38, 47, 48, 54, 56

[56] References Cited

U.S. PATENT DOCUMENTS

| | | |
|---|---|---|
| 33,908 | 12/1861 | Tilley . |
| 1,015,796 | 1/1912 | Gerlach . |
| 2,178,818 | 11/1939 | Earp-Thomas . |
| 2,243,192 | 5/1941 | Clark .............................. 34/136 |
| 2,823,106 | 2/1958 | Pierson . |
| 2,864,672 | 12/1958 | Brooks, Sr. . |
| 4,824,028 | 4/1989 | Rota ................................ 241/74 |

Primary Examiner—Michael G. Wityshyn
Assistant Examiner—William H. Beisner
Attorney, Agent, or Firm—Jacobson, Price, Holman & Stern

[57] ABSTRACT

An organic digesting system incorporating a pair of digester units each of which includes an elongated, horizontally disposed frusto-conical, stationary outer drum with each outer drum including a correspondingly frusto-conical inner drum that is rotatably driven about a horizontal axis. The outer upper drum includes an inlet at the smaller end thereof and a vertical discharge conduit at the larger end thereof which communicates with the smaller end of the lower outer drum. The larger end of the lower outer drum includes a discharge outlet or conduit. Each of the inner conical drums is constructed of foraminous material to form a periphery that is porous with the foraminous periphery of the inner drum being supported from support shafts at each end thereof. The interior of the inner drum is provided with a plurality of inwardly extending agitation blades which are spaced peripherally on the interior of the inner drum and arranged in longitudinally spaced arrays. Also, each inner drum is provided with a plurality of outwardly extending outer agitation blades with the function of these blades being to mix, agitate and churn the organic material while lifting and moving it from the entrance to the upper outer drum to the discharge into the lower outer drum and to the discharge outlet from the lower outer drum.

10 Claims, 2 Drawing Sheets

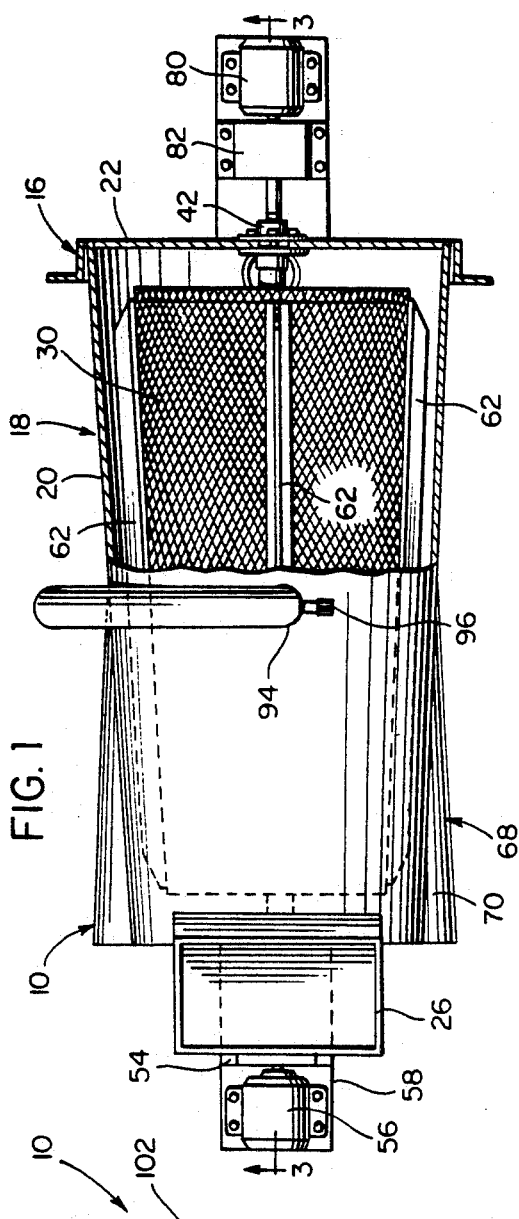
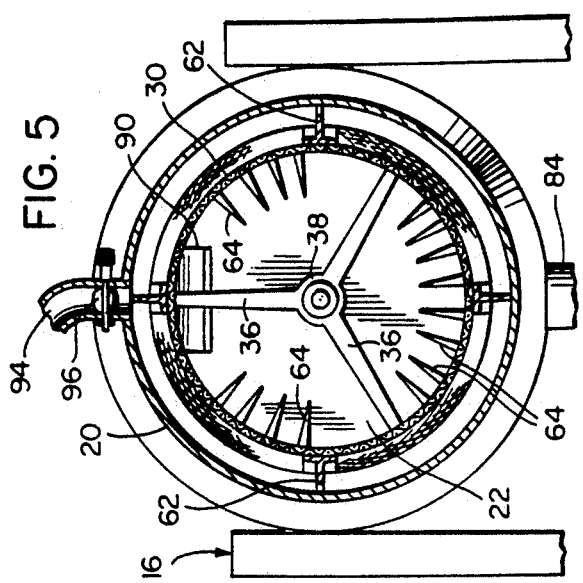
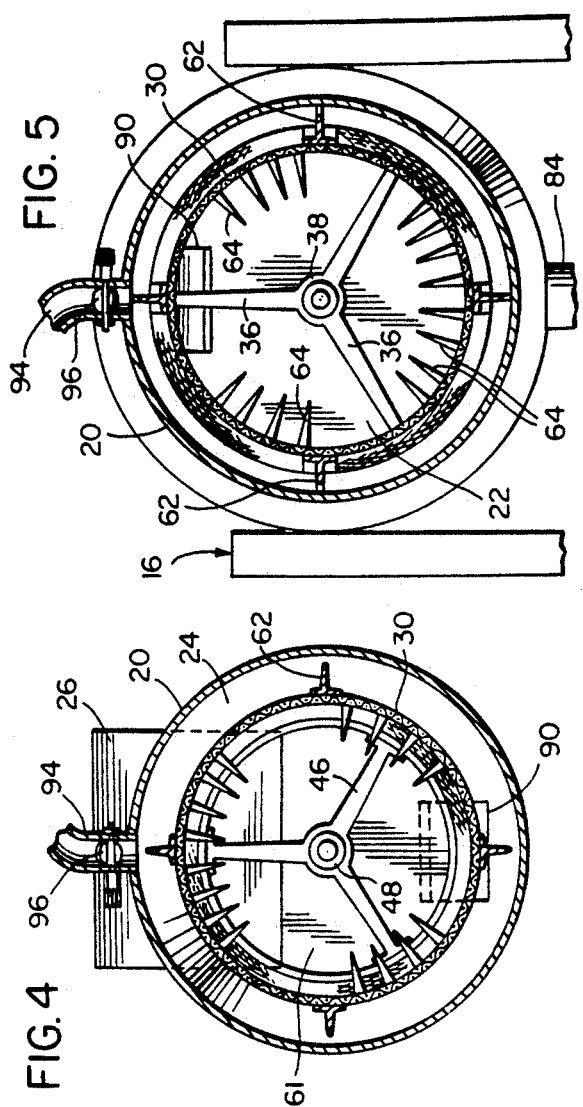
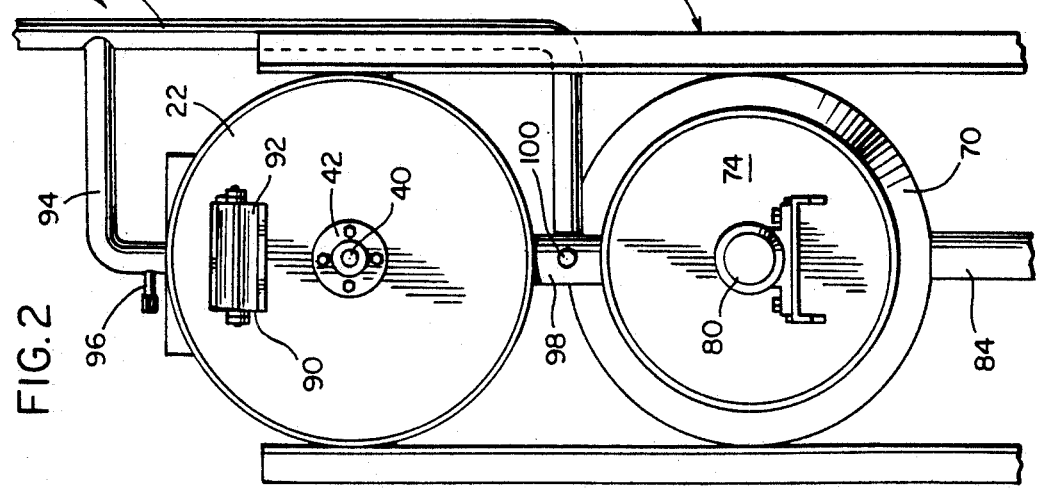

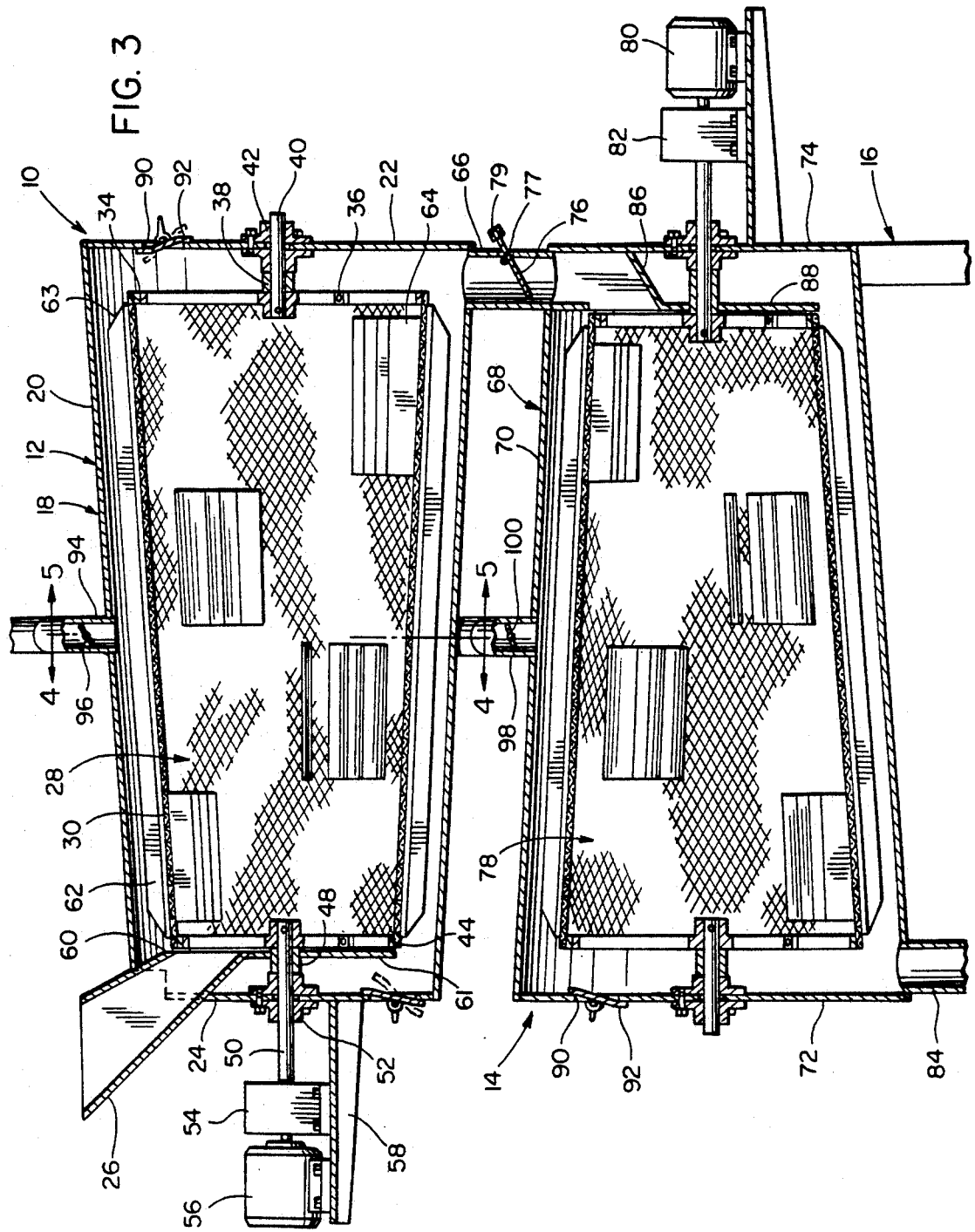

ORGANIC DIGESTING SYSTEM

BACKGROUND OF THE INVENTION

1. Field of the Invention

The present invention generally relates to an organic digesting system incorporating a pair of digester units each of which includes an elongated, horizontally disposed frusto-conical, stationary outer drum with each outer drum including a correspondingly frusto-conical inner drum that is rotatably driven about a horizontal axis. The outer upper drum includes an inlet at the smaller end thereof and a vertical discharge conduit at the larger end thereof which communicates with the smaller end of the lower outer drum. The larger end of the lower outer drum includes a discharge outlet or conduit. Each of the inner conical drums is constructed of foraminous material to form a periphery that is porous with the foraminous periphery of the inner drum being supported from support shafts at each end thereof. The interior of the inner drum is provided with a plurality of inwardly extending agitation blades which are spaced peripherally on the interior of the inner drum and arranged in longitudinally spaced arrays. Also, each inner drum is provided with a plurality of outwardly extending outer agitation blades with the function of these blades being to mix, agitate and churn the organic material while lifting and moving it from the entrance to the upper outer drum to the discharge into the lower outer drum and to the discharge outlet from the lower outer drum.

2. Description of the Prior Art

U.S. Pat. No. 2,864,672 discloses an organic waste reduction apparatus incorporating a pair of stationary outer drums which are oriented one above the other with the drums being frusto-conical in configuration and including an entrance at the smaller end of the upper drum, a discharge from the larger end of the upper drum into the smaller end of the lower drum and a discharge from the larger end of the lower drum with agitating devices being rotatably supported in each of the drums and driven about a horizontal axis. The following U.S. patents also relate to this field of endeavor.

33,908
1,015,796
2,178,818
2,823,106

U.S. Pat. No. 33,908 discloses a structure for rotating a drum or barrel but is not relevant to the structure and function of the present invention. U.S. Pat. No. 1,015,796 discloses a drying apparatus having a rotatable drum with projecting blades thereon that is for a totally different function as compared to the present invention. U.S. Pat. No. 2,178,818 discloses a digester for organic waste that includes a structure that is totally different from that of the present invention. U.S. Pat. No. 2,823,106 discloses a process of fermenting waste which involves a rotatable drum used to screen composted material at the end of the composting process. The device disclosed in U.S. Pat. No. 2,823,106 is entirely different in mechanical apparatus and principle of operation as compared to this invention.

None of the above discussed prior patents discloses the drum arrangements of this invention including a frusto-conical shape and the most necessary thermo-chambers for a closed vessel technique including the inner conical drums of screen material having an interior array of blades and an exterior array of blades associated with the inner rotatable drum. This structure and the treatment procedure of organic material provides an efficient digesting system requiring a minimum of power to operate that is accomplished by the use of gravity in assisting movement of the organic material through the digesting system.

SUMMARY OF THE INVENTION

An object of the present invention is to provide an organic digesting system providing a unique mechanical structure which interacts with the organic material being digested for efficient aeration and temperature controls necessary for proper inoculation, pasteurization and drying.

Another object of the invention is to provide an organic digesting system incorporating a pair of horizontally disposed, stationary outer drums or thermo-chambers receiving rotatable inner drums of porous material positioned therein which are driven about a horizontal axis with the drums being oriented one above the other for gravity flow with the drums being frusto-conical in configuration with the rotatable inner drums lifting and agitating the material and assisting in flow of material from an entry in the upper stationary drum to a discharge from the lower stationary drum.

A further object of the invention is to provide an apparatus in accordance with the preceding object in which the rotatable inner drums are constructed of screen material and provided with inwardly and outwardly extending blades for agitating and lifting material being digested with the frusto-conical configuration of the drums assisting in movement of the material through the apparatus by utilizing forces of gravity thereby reducing the power requirements for rotatably driving the inner drums.

Still another object of the invention is to provide an apparatus in accordance with the preceding objects which incorporates an aeration process with damper controls which aids in the aeration process as the organic material is lifted and agitated with waste gases associated with the process being controlled and capable of movement from the lower drum and upper drum through an exhaust conduit which controls the exit of waste gases and also controls aeration and temperature necessary for operation of the process.

A still further object of the invention is to provide an organic digesting system of relatively simple but unique mechanical construction utilizing gravity feed and conveyance of material combined with driven rotatable porous frusto-conical drums requiring minimum power for effective operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a top plan view, with portions broken away, illustrating the structure of the organic digesting system of the present invention.

FIG. 2 is an end elevational view of the invention.

FIG. 3 is a longitudinal, sectional view taken substantially upon a plane passing along section line 3—3 on FIG. 1 illustrating the structural arrangement of the components of the organic digesting system of this invention.

FIG. 4 is a transverse, sectional view, taken substantially upon a plane passing along section line 4—4 on FIG. 3 illustrating the structural details of the smaller end of the upper drum.

FIG. 5 is a transverse, sectional view, taken substantially upon a plane passing along section line 5—5 on FIG. 3 illustrating the structural details of the larger end of the upper drum.

DETAILED DESCRIPTION OF THE PREFERRED EMBODIMENT

Referring now specifically to the drawings, the organic digesting system of the present invention is generally designated by reference numeral 10 and is illustrated in overall configuration in FIGS. 1-3. The organic digesting system 10 includes an upper drum assembly 12 and a lower drum assembly 14 which are oriented generally in vertical alignment and are horizontally disposed and supported by any suitable frame structure generally designated by reference numeral 16.

The upper drum assembly 12 includes a horizontally disposed, frusto-conical outer drum or housing 18 which is stationarily supported from the frame structure 16 in any suitable manner and including a peripheral wall 20 and an end wall 22 at the larger end of the drum or housing 18 and an end wall 24 at the smaller end thereof. The end wall 24 and adjacent portion of the peripheral wall 20 is provided with an inlet hopper or chute 26 by which the organic material to be digested enters the upper drum assembly 12. Positioned interiorly of the outer drum 18 or housing is an inner rotatable drum 28 of frusto-conical configuration generally corresponding to and being concentric with the outer drum 18. The inner drum 28 includes a peripheral wall 30 of foraminous material such as metal screen, perforated metal grating or the like with the larger end of the inner drum 28 including a peripheral support ring 34 and radial support arms 36 rigid therewith and including a hub 38 at the center of the large end of the inner drum 28 thus forming a support spider for the peripheral wall 30. A support stub shaft 40 is received in the hub and rotatably journaled in a bearing structure 42 in the end wall 22. The smaller end of the inner drum 28 includes a similar peripheral support ring 44, support arms 46 and a central hub 48 mounted on a support stub shaft 50 journaled in a bearing 52 in the end wall 24 and extending from a reduction gear unit 54 driven by a motor 56 supported on a bracket 58 mounted on the end wall 24 thus rotating the inner drum 28 about a horizontal axis defined by the shafts 40 and 50. Other than the support spider for each end of the inner drum 28, the ends of the inner drum 28 are open. As illustrated in FIG. 3, the chute 26 includes an open end 60 which is closely associated with the upper portion of the open smaller end of the inner drum 28 and an end wall deflection plate 61 closing the lower portion of the open end of drum 28.

As illustrated in FIGS. 1 and 3-5, the exterior of the inner drum 28 is provided with a plurality of longitudinally extending blades 62 that are rigid with the outer surface of the inner drum 28 by being mounted on the peripheral wall 30 with the blades extending substantially throughout the entire length of the inner drum and provided with inclined end edges 63. The blades 62 extend radially from the peripheral wall 30 and the outer edges thereof terminate adjacent to but in spaced relation to the inner surface of the peripheral wall 20 of the stationary outer drum 18 as illustrated in FIGS. 4 and 5.

The inner drum 28 also includes a plurality of relatively short, inwardly extending blades 64 which are arranged in circumferentially spaced arrays and longitudinally spaced arrays as illustrated in FIGS. 3-5 with these blades extending inwardly more or less one-half of the radius of the inner drum for lifting and agitating the material within the inner drum 28.

As illustrated in FIG. 3, the upper drum assembly 12 is positioned above and generally in alignment with the lower drum assembly 14 and the larger end of the upper drum 18 includes a discharge outlet or conduit 66 which communicates with the smaller end of a lower outer drum or housing 68 which is the same shape and size as the upper stationary drum 18 except that the peripheral wall 70 is oriented oppositely to the wall 20 with the larger end 72 of the lower drum being generally aligned with the smaller end 24 of the upper drum 18 and the smaller end wall 74 is aligned with the larger end wall 22 of the upper stationary drum 18. The discharge conduit 66 extends from the larger end of the peripheral wall 20 into the smaller end of the peripheral wall 70 with a pivotal damper or valve 76 being provided in the conduit 66 to control flow of material from the upper drum assembly 12 into the lower drum assembly 14. An inner porous drum generally designated by reference numeral 78 of the same frusto-conical shape as the outer drum 68 is positioned therein and is duplicative of the structure of the upper inner drum 28 except that the frusto-conical configuration is reversed with the drive motor 80 and reduction gear unit 82 being located at the end of the lower drum assembly 14 in opposite relation to the location of the motor 56 and reduction gear unit 54 in the upper drum assembly. The structure and operation of the lower rotatable inner drum 78 is the same as the upper rotatable drum 28 except that the frusto-conical configuration is reversed and corresponds with the lower stationary drum or housing 68. The large end of the peripheral wall 70 of the lower stationary drum 68 is provided with a discharge outlet or conduit 84 for discharge of material from the lower stationary drum 68. Also, the smaller end wall 74 of the lower stationary drum 68 is provided with an inclined baffle 86 extending inwardly and downwardly from the end wall 74 to deflect material entering the lower drum 68 from the conduit 66 into the rotatable inner drum 78 with a retaining plate 88 forming a closure for the lower open end portion of the smaller end of the lower drum 78 to retain the material therein in a manner similar to the plate 61 associated with the smaller end wall of the rotatable inner drum 28 in the upper drum assembly 12.

Each of the large end walls 22 and 72 includes an opening 90 having a damper 92 pivotally mounted therein to control the effective size of the opening 90. Extending upwardly from the center of the upper drum peripheral wall 20 is an exhaust stack 94 provided with a damper 96. Likewise, an exhaust stack 98 is connected to the upper portion of the peripheral wall 70 of the lower stationary drum 68 with the exhaust stack 98 also including a damper 100 mounted therein. The exhaust stacks 94 and 98 are connected to a vertical exhaust pipe 102 as illustrated in FIG. 2.

As illustrated, each of the upper and lower digesting units of the digesting system 10 includes an elongated, horizontal, stationary frusto-conical drum or housing with end walls with the smaller end of the upper drum assembly 12 including an entrance chute or conduit for the organic material which may include some stalks and other material and a discharge conduit is provided at the bottom of the large end of each unit. While two units have been illustrated, it is within the purview of this invention to include a single or any number of digester units. Also, each of the stationary drums includes an inner drum supported by drive and support shafts and driven by a suitable motor with each inner drum including a peripheral wall of screen material supported at its ends from the support shafts by a spider-type support. The inner drums are generally of the same frusto-conical configuration as the outer stationary drums and includes a plurality of inner agitating blades 64 oriented in longitudinally and circumferentially spaced arrays with the size, shape and positioning of the inner blades being varied depending upon the materials being digested. Also, the exterior surface of each inner drum is provided with outer agitation blades 62 in which the spacing and length configuration as well as the radial configuration and dimension of the blades can vary with the function of the blades being to mix, agitate and churn the organic material while lifting and moving it from the entrance chute to the exit conduit. As illustrated, the agitation blades on the interior are spaced longitudinally and parallel with the center line of the support shafts. Preferably, the blades 64 are arranged in groups which are spaced in a staggered configuration such as in a worm gear configuration which provides a mechanism for moving the organic material from the entrance end to the discharge conduit somewhat similar to a spiral screw or auger. The shape of the drums in this system and the rotational action of the inner drums provides to some extent a gravity feed thus reducing the power requirements for driving the inner drums.

The openings 90 with the dampers 92 which can be counterweighted control the size of the openings 90 to provide an air inlet for the system. Blowers may be optionally provided to aid in the aeration process as the organic stalk or other material is lifted and agitated. The discharge conduit 66 between the upper and lower drum assemblies is provided with an upwardly swinging baffle plate 76 which is suitably hinged at 77 which separates the decomposition gases in the upper drum assembly from the decomposition gases in the lower drum assembly. An external counterweight 79 is provided for the baffle plate 76 to allow material being digested to pass from the upper digester unit to the lower digester unit while preventing waste gases associated with the process from exiting from the lower digesting unit or drum to the upper digester unit or drum. This arrangement along with the exhaust stacks 94 and 98 and associated dampers 96 and 100 provide an even draft that can easily control not only the exit of decomposition gases through the exhaust stacks but also provides all of the aeration and temperature controls necessary for the inoculation, pasteurization and drying variables for proper operation of the process.

The organic digesting system of this invention is unique in its operation due to the interaction of the mechanical structural components with the material being digested. As material enters the entrance conduit or chute 26, it is deflected by the chute 26 and the plate 61 into the inner rotational drum 28. The lighter and finer particles are separated from larger and rougher stalk material due to the porous or screen construction of the peripheral wall 30 of the inner drum 28. This separation is significant because the finer particles ar usually saturated with liquids while the larger particles are dryer internally but yet need to be broken up. The construction of the blades lifts the separated particles upwardly by rotational movement of the outer blade 62 and the inner blades 64. This allows the larger stalks to tumble more freely inside the inner drum 28 while the finer particles aerate more efficiently between the outer surface of the inner drum 28 and the edge of the agitation blades 62 before being reintroduced into the upper portion of the porous inner drum 28 and again sifted through the central portion of the rotatable inner drum 28. The above interaction is continuous throughout the system while exhaust gases can exit through the damper controlled exhaust stacks 94 and 98.

The entire outer drum or housing 18 serves not only as a housing for the mechanical operation but it also provides a containment for the finer particles, acts as a hood for waste gases and forms a thermochamber to provide a desired actuating temperature for insuring the pasteurization, inoculation and drying processes to occur. This is accomplished by enabling a large volume of material to be digested in a horizontal gravity-fed system which requires relatively small power requirements for rotating the inner drums with more effective results due to separation of finer particles from coarse particles and treating these particles separately in multiple stages while controlling flow of decomposition gases and temperature thereby providing an effective digesting system.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. An organic digesting system comprising a stationary substantially horizontal outer drum having end walls forming an enclosure, inlet means at one end of the drum for introducing material to be digested, outlet means at the bottom of the drum remote from the inlet means for discharge of digested material, an inner rotatable drum mounted within the stationary drum in generally concentric relation thereto, means journaling the inner drum from the stationary drum for rotation about a generally horizontal axis, means rotatably driving said inner drum, said inner drum including a porous peripheral wall and open ends spaced from the end walls of the stationary drum, means guiding material to be digested from the inlet means into the open end of the inner drum adjacent thereto, the outlet means in the outer drum being located at the open end of the inner drum remote from the inlet means, said inner drum including a plurality of outwardly extending blades thereon and a plurality of inwardly extending blades thereon for lifting and agitating organic material being digested with the finer particles of material passing through the porous peripheral wall of the inner drum and being lifted and agitated by the outer blades with the finer particles being lifted by the outer blades and passing back through the porous peripheral wall into the interior of the rotating drum for subsequent sifting through the coarser material retained interiorly of the inner drum and ultimately being discharged through the outlet means, the blades on the interior of the inner drum lifting and tumbling coarser particles for agitation and forming smaller particles from the coarser particles, said blades on the interior of the inner drum including a plurality of circumferentially and longitudinally spaced arrays of blades for sequential lifting and tumbling of the coarser material being digested.

2. The organic digesting system as defined in claim 1 further comprising air inlet means for allowing air into said stationary drum, and means controlling the inlet of air in the air inlet means.

3. The organic digesting unit defined in claim 2 further comprising an exhaust stack for decomposition gases at an upper portion of the stationary drum, baffle means controlling discharge of decomposition gases from the stationary drum, said outlet means including a pivotal counterweighted baffle enabling discharge of digested material while controlling reverse flow through the outlet means.

4. The organic digesting system as defined in claim 1 wherein said outer drum and inner drum are of frusto-conical configuration each having small and large ends, the inlet means being disposed at the smaller ends of the inner and outer drums, the open ends of the inner drum including a support spider having centrally disposed, longitudinally extending support and drive shaft means engaged with the end walls of the outer drum for permitting rotation of the inner drum within the outer drum, said means rotating the inner drum including a power unit connected to the support and drive shaft means.

5. The organic digesting system as defined in claim 4 wherein said blades on the exterior of the inner drum are circumferentially spaced and extend in substantially a straight line condition throughout the length of the inner drum with the radial outer edges of the blades being spaced from the interior of the outer drum.

6. The organic digesting system as defined in claim 5 wherein the inwardly extending blades on the inner drum are arranged in spirally oriented arrays to assist in moving material being digested toward the larger end of said drums for discharge through said outlet means.

7. The organic digesting system as defined in claim 6 wherein said means guiding material into the inner drum includes a plate forming a closure for the smaller end of the inner drum, and a chute connected to an upper edge of said plate.

8. The organic digesting system as defined in claim 7 further comprising a second stationary drum and a second rotatable inner drum each of the same construction as the first mentioned inner and outer drums, respectively, and being of a frusto-conical shape having small ends and large ends, the second stationary drum and second inner drum being oriented vertically below the first mentioned drums with the large ends of the lower drums being aligned with the small ends of the upper drums, wherein the outlet means of said first stationary drum is connected with the inlet means of said second stationary drum.

9. The organic digesting system as defined in claim 8 further comprising a second exhaust stack for decomposition gases and second baffle means controlling discharge of decomposition gases connected to the top central portion of the second stationary drum.

10. An organic digesting system comprising a non-rotatable housing having end walls forming an enclosure, gravity feed digestible material inlet means adjacent one end of the housing for introducing material to be digested, digested material outlet means adjacent the bottom of the housing remote from the inlet means for discharge of digested material, a rotatable drum mounted within the housing, means journaling the drum from the housing for rotation about a generally longitudinal axis, means rotatable driving said drum, said drum including a porous peripheral wall and open ends spaced from the end walls of the housing, means guiding material to be digested from the inlet means into the open end of the drum adjacent thereto, the outlet means in the housing being located adjacent the open end of the drum remote from the inlet means, said peripheral wall of the drum including a plurality of outwardly extending blades thereon and a plurality of inwardly extending blades thereon for lifting and agitating organic material being digested with the finer particles of material passing through the porous peripheral wall of the drum when being lifted and agitated by the blades, the finer particles within the housing being lifted by the outer blades and passing inwardly through the porous peripheral wall into the interior of the rotating drum for subsequent sifting through coarser material retained interiorly of the drum by the porous peripheral wall with the first particles of material ultimately being discharged through said outlet means, the blades on the interior of the drum lifting and tumbling finer particles and coarser particles within the drum for agitation and forming finer particles from the coarser particles with the finer particles passing through porous peripheral wall into the housing for ultimately being discharged through said outlet means, air inlet means and gas outlet means in said housing to permit inflow of air and outflow of decomposition gases, respectively, means controlling inflow of air through said air inlet means, and means controlling outflow of decomposition gases through said gas outlet means for controlling aeration and temperature conditions within the housing and drum for digesting the material.

* * * * *